(12) United States Patent
Schwingendorf et al.

(10) Patent No.: US 9,622,901 B2
(45) Date of Patent: *Apr. 18, 2017

(54) SLEEPY HEADS NECK PILLOW

(75) Inventors: Alice Jean Schwingendorf, Tokyo (JP); Gabriel Olivier Durand, Tokyo (JP)

(73) Assignees: Alice Jean Schwingendorf, Tokyo (JP); Gabriel Olivier Durand, Tokyo (JP)

( * ) Notice: Subject to any disclaimer, the term of this patent is extended or adjusted under 35 U.S.C. 154(b) by 32 days.

This patent is subject to a terminal disclaimer.

(21) Appl. No.: 13/635,776

(22) PCT Filed: Feb. 10, 2011

(86) PCT No.: PCT/JP2011/000779
§ 371 (c)(1),
(2), (4) Date: Nov. 14, 2012

(87) PCT Pub. No.: WO2011/118120
PCT Pub. Date: Sep. 29, 2011

(65) Prior Publication Data
US 2013/0047342 A1 Feb. 28, 2013

Related U.S. Application Data

(63) Continuation-in-part of application No. 12/659,814, filed on Mar. 22, 2010, now Pat. No. 8,141,187.

(51) Int. Cl.
*A61F 5/37* (2006.01)
*B60N 2/48* (2006.01)

(52) U.S. Cl.
CPC .......... *A61F 5/3707* (2013.01); *B60N 2/4879* (2013.01); *B60N 2/4882* (2013.01)

(58) Field of Classification Search
CPC ...... A47G 9/10; A47G 9/1081; A47G 9/1009; A47C 7/383; A47C 20/00; A47C 7/38; A47C 7/42

(Continued)

(56) References Cited

U.S. PATENT DOCUMENTS 1,510,187 A 9/1924 Martin
1,579,585 A 4/1926 Wieder et al.
(Continued)

FOREIGN PATENT DOCUMENTS

AU 8872501 A 4/2002
CN 101166446 A 4/2008
(Continued)

OTHER PUBLICATIONS

Chinese communication, with English translation, issued Sep. 9, 2013 in corresponding Chinese patent application No. CN 201180015188.1.

(Continued)

*Primary Examiner* — Robert G Santos
*Assistant Examiner* — Myles Throop
(74) *Attorney, Agent, or Firm* — Nields, Lemack & Frame, LLC

(57) ABSTRACT

The present invention is related to a supportive sleepy heads neck pillow comprising a pillow with a bone structure support inside the pillow and a clip/strap system that is fixed to the bone structure, wherein the bone structure support is fully incased in the pillow, and the bone structure support comprises three parts, which may be adjustable; a neck bone support, an arm bone, and an upper back bone. The invention can also be used awake for comfort and support while relaxing, watching TV, playing video games, gambling, etc. It can also be used for head and neck support for people who have neck injuries, or to prevent neck injuries during transportation.

10 Claims, 14 Drawing Sheets

(58) Field of Classification Search
USPC ............ 5/633, 636, 637, 639, 640, 643, 645
See application file for complete search history.

(56) References Cited

U.S. PATENT DOCUMENTS

| | | | |
|---|---|---|---|
| 2,638,152 A * | 5/1953 | Pulsifer | 297/400 |
| 3,029,107 A * | 4/1962 | Myers | 297/399 |
| 3,285,658 A | 11/1966 | Cleveland | |
| 4,285,081 A | 8/1981 | Price | |
| 4,345,347 A | 8/1982 | Kantor | |
| 4,562,833 A | 1/1986 | Pujals, Jr. | |
| 4,617,691 A | 10/1986 | Monti et al. | |
| 4,708,129 A | 11/1987 | Pujals, Jr. | |
| 4,738,488 A | 4/1988 | Camelio | |
| 4,815,154 A * | 3/1989 | Grimes | 5/657 |
| D322,380 S | 12/1991 | Asir | |
| D334,159 S | 3/1993 | Mulligan | |
| 5,505,523 A * | 4/1996 | Wang | 297/393 |
| 5,778,469 A | 7/1998 | Festa | |
| D396,594 S | 8/1998 | Lefebvre | |
| 5,868,471 A * | 2/1999 | Graham et al. | 297/397 |
| D413,751 S | 9/1999 | Alyea | |
| 5,974,607 A | 11/1999 | Smith | |
| D420,845 S | 2/2000 | Rumage | |
| 6,123,389 A | 9/2000 | O'Connor et al. | |
| 6,305,749 B1 | 10/2001 | O'Connor et al. | |
| 6,786,554 B1 | 9/2004 | Zahiri | |
| D503,062 S | 3/2005 | Nash | |
| 6,893,094 B2 | 5/2005 | O'Connor | |
| D522,300 S | 6/2006 | Roberts | |
| D531,424 S * | 11/2006 | Kusachi | D6/367 |
| 7,197,781 B2 | 4/2007 | Ramsbottom et al. | |
| 7,204,557 B1 * | 4/2007 | Burton | 297/397 |
| 7,393,057 B2 * | 7/2008 | Fraser | 297/392 |
| D592,310 S * | 5/2009 | Leatt | D24/191 |
| 7,547,071 B2 * | 6/2009 | Huffman | 297/397 |
| 7,644,990 B2 | 1/2010 | Pearson | |
| D619,402 S | 7/2010 | Sternlight et al. | |
| 7,908,692 B2 | 3/2011 | Lange | |
| 8,141,187 B2 | 3/2012 | Schwingendorf et al. | |
| D664,799 S | 8/2012 | Schwingendorf et al. | |
| D665,212 S | 8/2012 | Schwingendorf et al. | |
| 8,418,293 B2 * | 4/2013 | Tansingco | 5/636 |
| 8,646,135 B2 | 2/2014 | Shamaiengar | |
| 8,650,684 B1 | 2/2014 | Mackinnon | |
| 8,739,336 B2 | 6/2014 | Kiefer | |
| 8,863,335 B2 | 10/2014 | Shamaiengar | |
| 8,898,840 B1 | 12/2014 | Majette | |
| 9,021,636 B2 | 5/2015 | Schwingendorf et al. | |
| 9,131,791 B2 | 9/2015 | Schwingendorf et al. | |
| 2001/0049844 A1 * | 12/2001 | Gilbert | 5/636 |
| 2001/0054837 A1 | 12/2001 | O'Connor | |
| 2005/0102758 A1 | 5/2005 | Ramsbottom et al. | |
| 2005/0179300 A1 * | 8/2005 | O'Connor et al. | 297/391 |
| 2006/0244300 A1 | 11/2006 | Watson Savage | |
| 2007/0056107 A1 * | 3/2007 | Gabriel | 5/639 |
| 2009/0013471 A1 | 1/2009 | Yang | |
| 2011/0094035 A1 | 4/2011 | Tansingco | |
| 2011/0225736 A1 | 9/2011 | Schwingendorf et al. | |
| 2012/0011655 A1 * | 1/2012 | Rojas | 5/636 |
| 2012/0030876 A1 | 2/2012 | Schwingendorf et al. | |
| 2012/0313417 A1 | 12/2012 | Hurwitz | |
| 2013/0333117 A1 | 12/2013 | Shamaiengar | |
| 2014/0115788 A1 | 5/2014 | Shamaiengar | |
| 2015/0157130 A1 | 6/2015 | Kellock et al. | |
| 2015/0216335 A1 | 8/2015 | Schwingendorf et al. | |
| 2015/0257554 A1 | 9/2015 | Ross et al. | |

FOREIGN PATENT DOCUMENTS

| | | |
|---|---|---|
| DE | 10196653 B | 12/2005 |
| GB | 2382985 A | 6/2003 |
| GB | 2382985 B | 4/2005 |
| JP | 2-80045 A | 3/1990 |
| JP | 3015207 U | 8/1995 |
| JP | 3024929 U | 6/1996 |
| JP | 2000-232928 A | 8/2000 |
| JP | 2002-325656 A | 11/2002 |
| JP | 2005-95472 A | 4/2005 |
| JP | D1455503 S | 10/2012 |
| WO | 02/24031 A1 | 3/2002 |
| WO | 2011/118120 A1 | 9/2011 |
| WO | 2013/042365 A1 | 3/2013 |

OTHER PUBLICATIONS

International Search Report mailed Apr. 26, 2011 in corresponding PCT application No. PCT/JP2011/000779.
International Search Report and Written Opinion mailed Dec. 25, 2012 in co-pending PCT application No. PCT/JP2012/005980.
Written Opinion mailed Apr. 26, 2011 in co-pending PCTapplication No. PCT/JP2011/000779.
International Preliminary Report on Patentability mailed Oct. 4, 2012 in co-pending PCTapplication No. PCT/JP2011/000779.
Notice of Allowance mailed Dec. 17, 2014 in co-pending U.S. Appl. No. 13/240,095.
Office Action mailed Aug. 21, 2014 in co-pending U.S. Appl. No. 13/240,095.
Office Action—Restriction—mailed Jun. 2, 2015 in co-pending U.S. Appl. No. 14/669,423.
Notice of Allowance mailed Jun. 22, 2015 in co-pending U.S. Appl. No. 14/669,423.
Notice of Allowance mailed Feb. 1, 2016 in co-pending U.S. Appl. No. 29/492,900.
Notice of Allowance mailed Dec. 11, 2015 in co-pending U.S. Appl. No. 29/492,900.

* cited by examiner

SLEEPY HEADS NECK PILLOW

This application is a §371 of International Application No. PCT/JP2011/000779 filed Feb. 10, 2011, which claims priority of U.S. patent application Ser. No. 12/659,814 filed on Mar. 22, 2010, the disclosures of which are hereby incorporated by reference.

FIELD OF THE INVENTION

The invention is a supportive heads neck pillow with a supportive bone structure inside the pillow. The invention is used for head and neck support, and comfort while sleeping sitting up during transportation.

BACKGROUND TO THE INVENTION

The reason we thought about this invention, it is because like us, and millions of other people can't sleep comfortably when sitting up during traveling (airplane, train, bus trip, and passenger in cars, etc.). Another reason we thought about this invention is because it is suitable for people who have neck injuries, it will help keep their head and neck secure during traveling (airplane, train, bus trip, and passenger in cars, etc.). It will also procure a great feeling of comfort. After research and testing many different heads neck pillows on the market, not one was satisfactory to give the support, and comfort while sitting up sleeping. We decided to invent a heads neck pillow that would have a great comfort, and with inside the pillow have a supportive bone structure that will conform, fit the shape of the neck with great support.

SUMARRY OF THE INVENTION

The sleepy heads neck pillow of the present invention is a new style supportive pillow that will give your neck, head and upper back support. It will give great comfort while sleeping while sitting up during transportation.

The invention is related to a supportive heads neck pillow with a supportive bone structure inside the pillow. The invention is used for head and neck support, and comfort while sleeping sitting up during transportation. It can also be used for head and neck support for people who have neck injuries, or to prevent neck injuries during transportation. The main components are made up of two things. That is, the pillow with the supportive bone structure inside it, which gives support and comfort to the head, neck, and upper back, and the supportive, adjustable straps which are connected to the adjustable clips which give the extra support to the pillow when connected to a seat.

That is, the invention has the following constitutions;

(1) A sleepy heads neck pillow comprising a pillow with a bone structure support inside the pillow and a clip/strap system that is fixed to the bone structure, wherein the bone structure support is fully incased in the pillow, and the bone structure support comprises three parts, which may be adjustable; a neck bone support, an arm bone, and an upper back bone.

(2) The sleepy heads neck pillow according to (1), wherein said clip/strap system comprises a supportive adjustable strap which is connected to the clip, said adjustable strap being fixed to said bone structure.

(3) The sleepy heads neck pillow according to (1) or (2), wherein the bone structure support is made of one piece.

(4) The sleepy heads neck pillow according to any one of (1) to (3), which is designed to be reversible wherein the top part of the pillow is used when being awake, to give support and comfort while using a computer, watching TV, playing a video game or the like, and bottom part of the pillow is used when sleeping while sitting up.

(5) A pillow configured to be positioned on the shoulders of a wearer and support the neck of the wearer, comprising:
a bone structure support fully incased inside said pillow, said bone structure support comprising a neck bone support configured to support the neck of the wearer, a pair of spaced arm bones extending from said neck bone support and configured to support the head of the wearer, and an upper back bone extending from said neck bone support and configured to support the back of the wearer.

(6) The pillow of (5), further comprising a strap system fixed to said bone structure support, said strap system comprising a clip.

(7) The pillow of (5) or (6), wherein said neck bone support is C-shaped.

(8) The pillow of any one of (5) to (7), wherein each of said arm bones are configured to extend over the shoulder of the wearer.

(9). The pillow of any one of (5) to (8), wherein said upper back bone is configured to extend from the neck down the upper back of the wearer.

(10) The pillow of any one of (5) to (9), further comprising shoulder support padding on said pillow configured to contact the wearer's shoulders.

(11) The pillow of any one of (5) to (10), further comprising a pillow cover covering said pillow.

(12) The sleepy heads neck pillow according to any one of (1) to (11), which is designed to be reversible wherein the top part of the pillow is used when being awake, to give support and comfort while using a computer, watching TV, playing a video game or the like, and bottom part of the pillow is used when sleeping while sitting up.

(13) A clip/strap system for a sleepy heads neck pillow, said clip/strap system configured to engage a seat having a front, back and a top, said clip/strap system comprising adjustable seat clips, adjustable seat straps, detachable clips and a supportive seat brace, wherein said adjustable seat clips comprise two pieces; a back clip configured to set on said back and top of said seat, and a front clip configured to set on said front and top part of said seat and continues as the supportive seat brace, and wherein said adjustable seat strap system is connected to said adjustable seat clips and said detachable clips which is connected to said pillow, and said detachable clips can separate said pillow from said adjustable seat clips.

DETAILED EXPLANATION OF THE INVENTION

Figure 1:
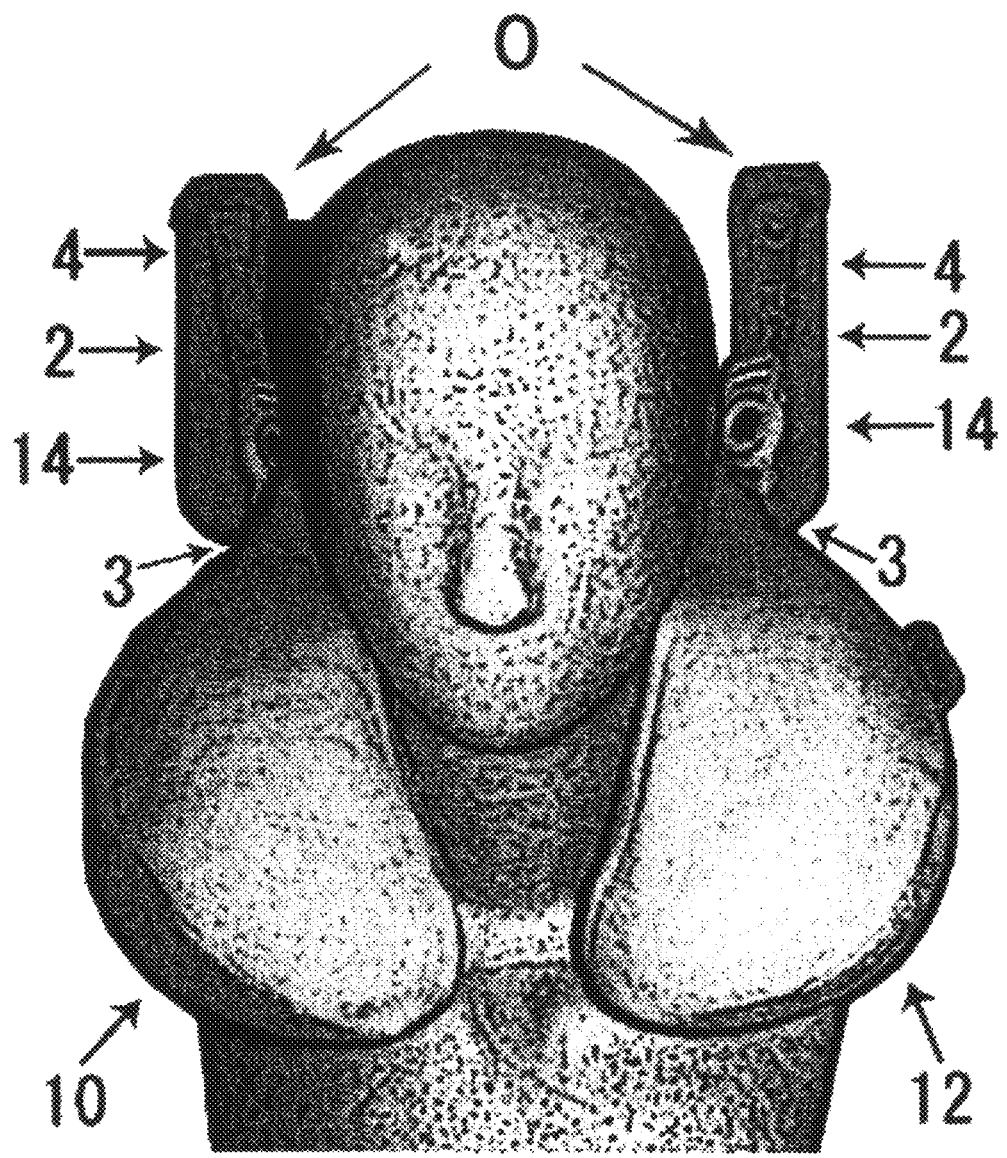
FIG. 1 shows a front view of Supportive Sleepy Heads Neck Pillow with Cover, Strap System and Bone Structure Support (0, 2, 3, 4, 10, 12, 14).
Figure 2:
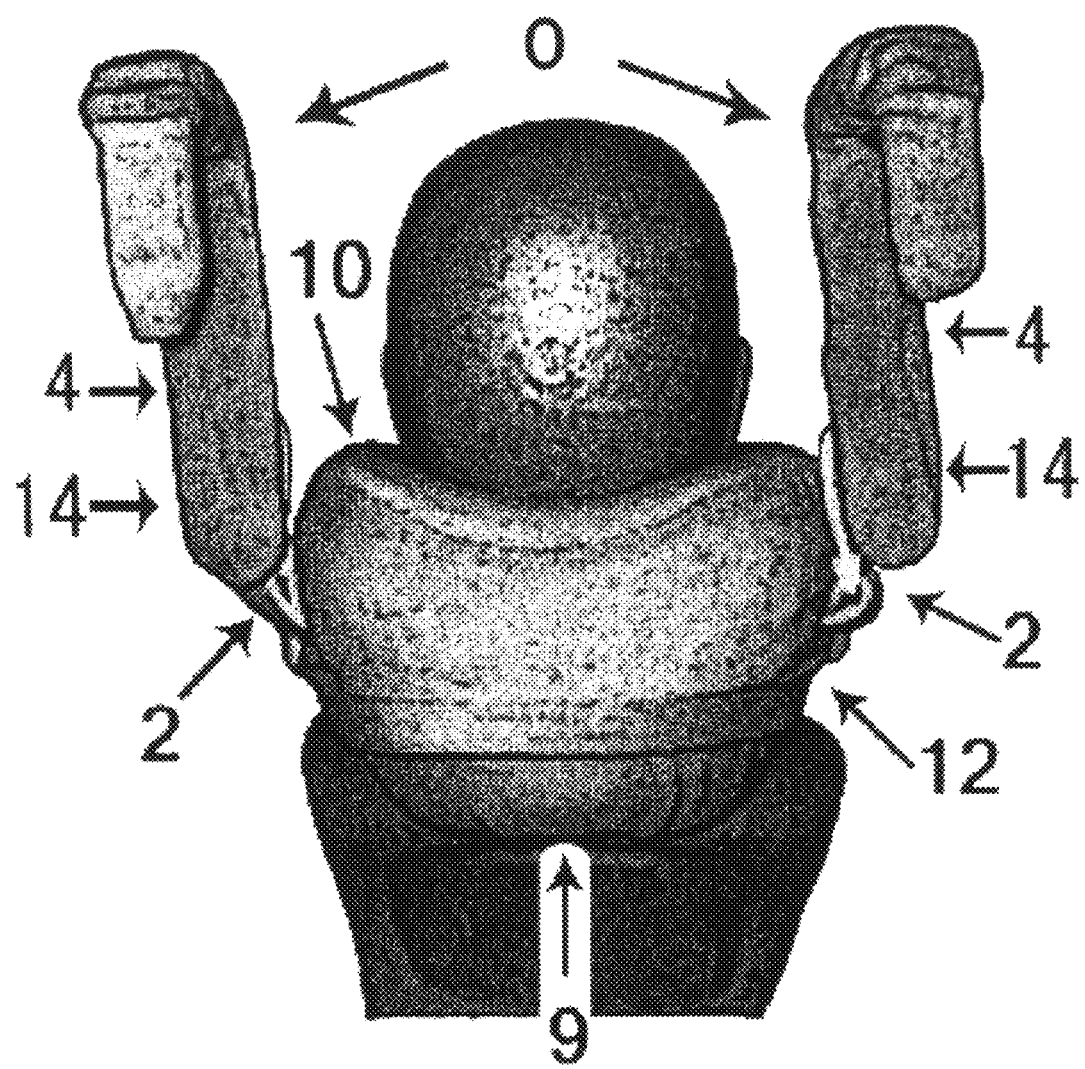
FIG. 2 shows a back view of Supportive Sleepy Heads Neck Pillow with Cover, Strap System and Bone Structure Support (0, 2, 4, 9, 10, 12, 14).
Figure 3:
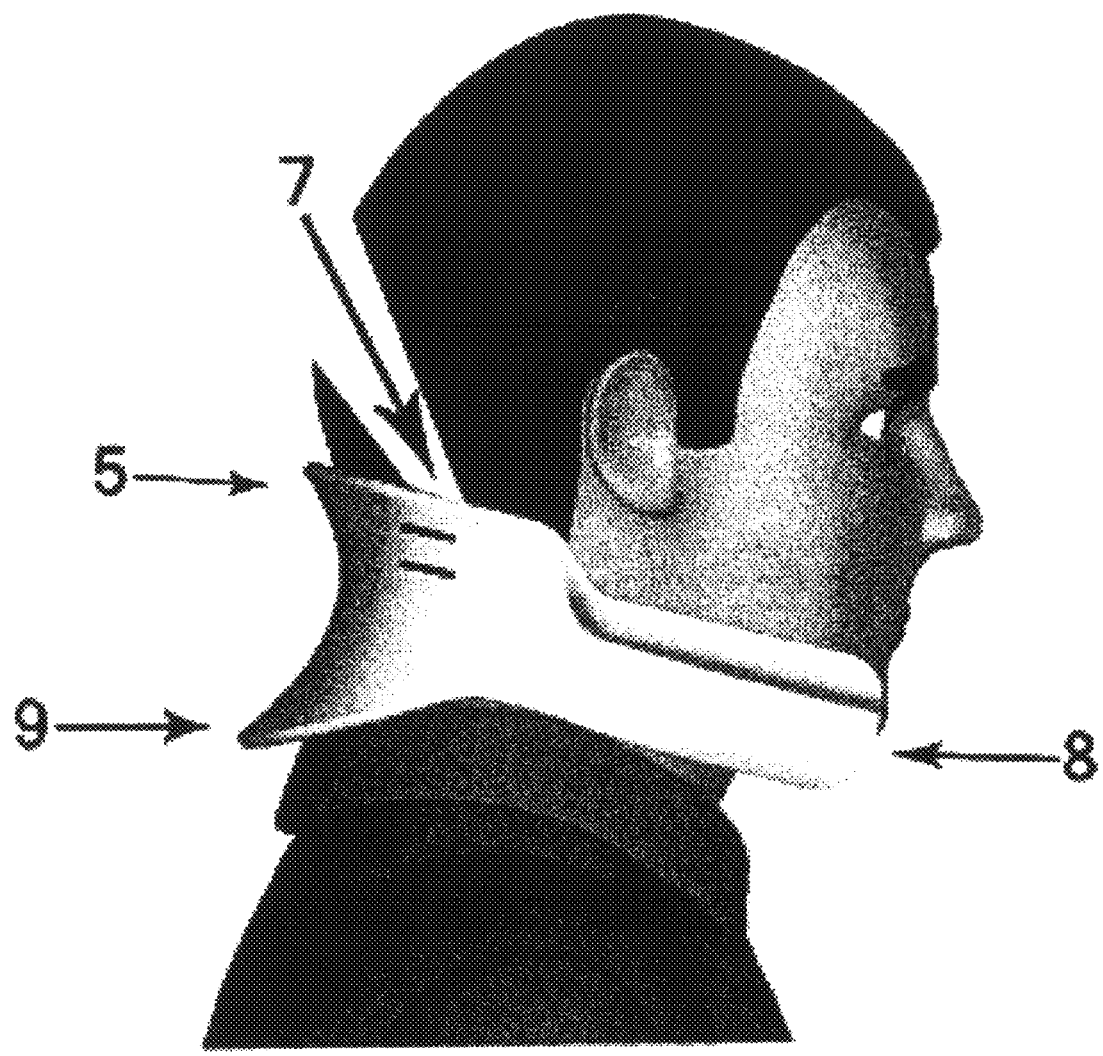
FIG. 3 shows a side view of Bone Structure Support (5, 7, 8, 9).
Figure 4:
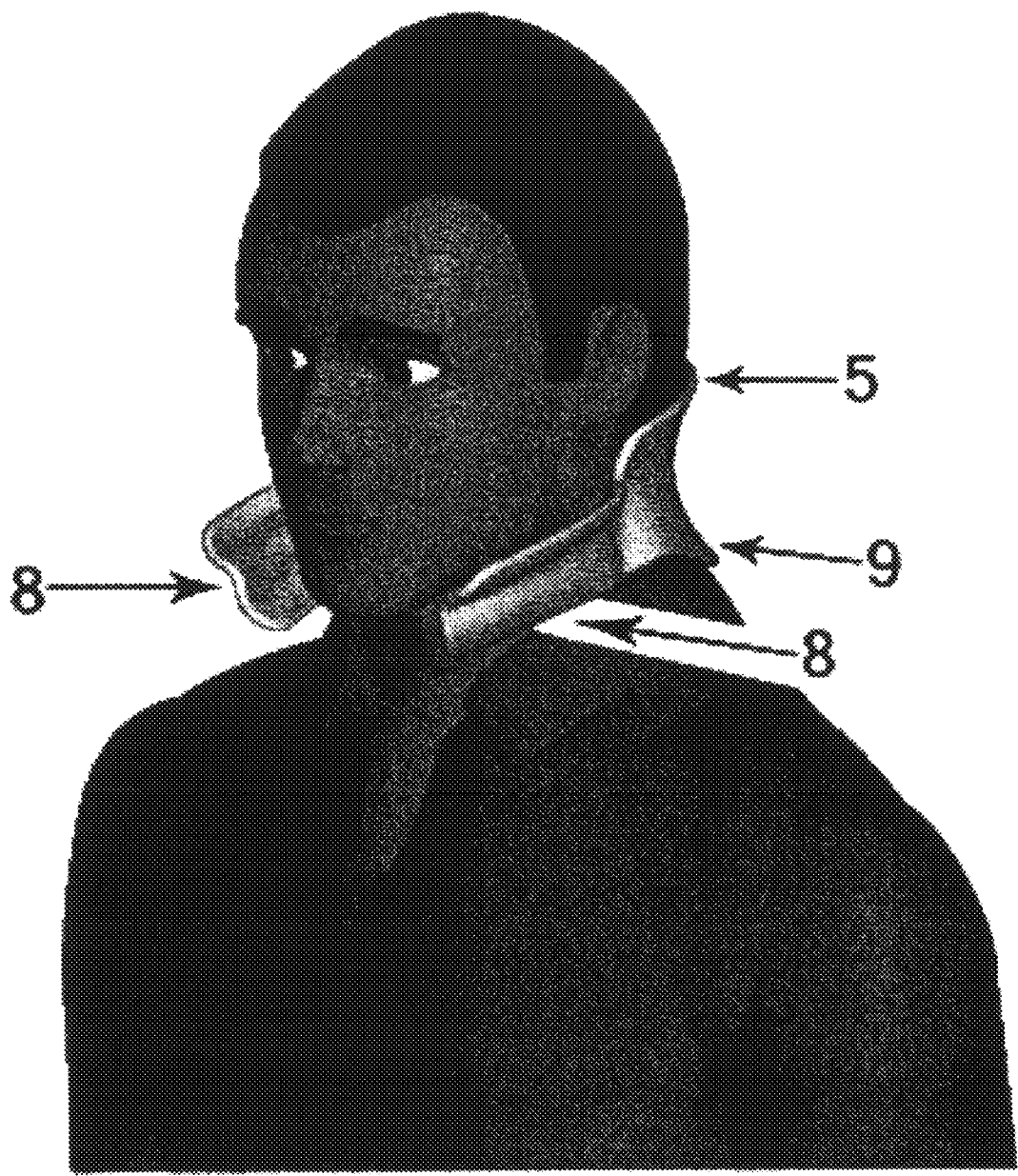
FIG. 4 shows ¾ side view of Bone Structure Support (5, 8, 9).
Figure 5:
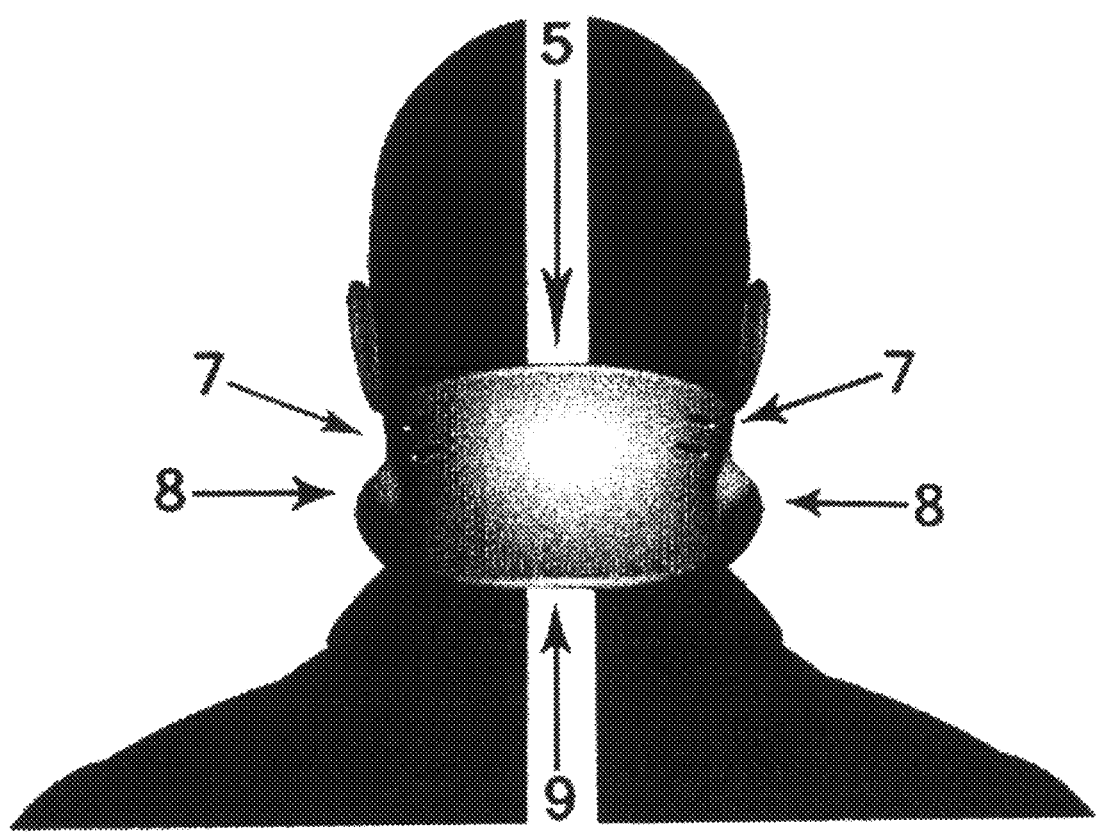
FIG. 5 shows a back view of Bone Structure Support (5, 7, 8, 9).
Figure 6:
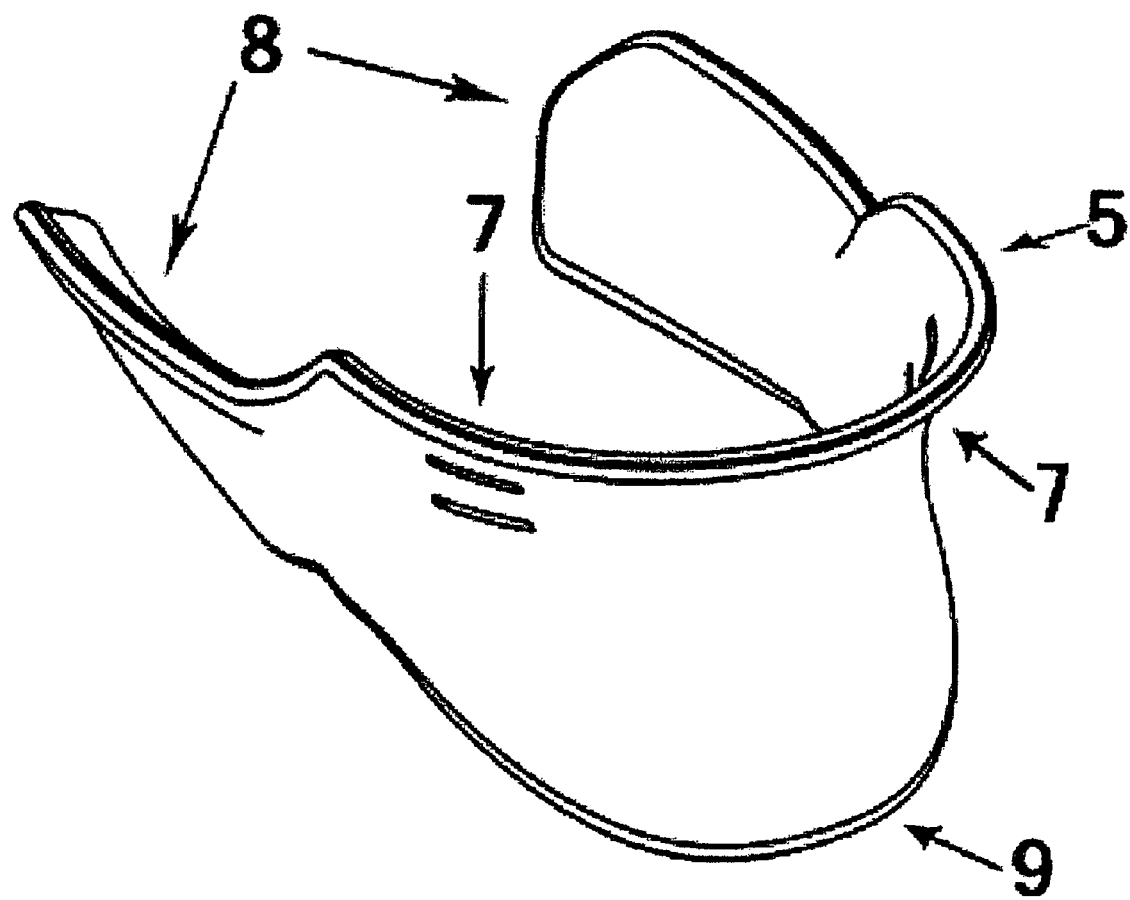
FIG. 6 shows a ¾ back view of Bone Structure Support (5, 7, 8, 9).
Figure 7:
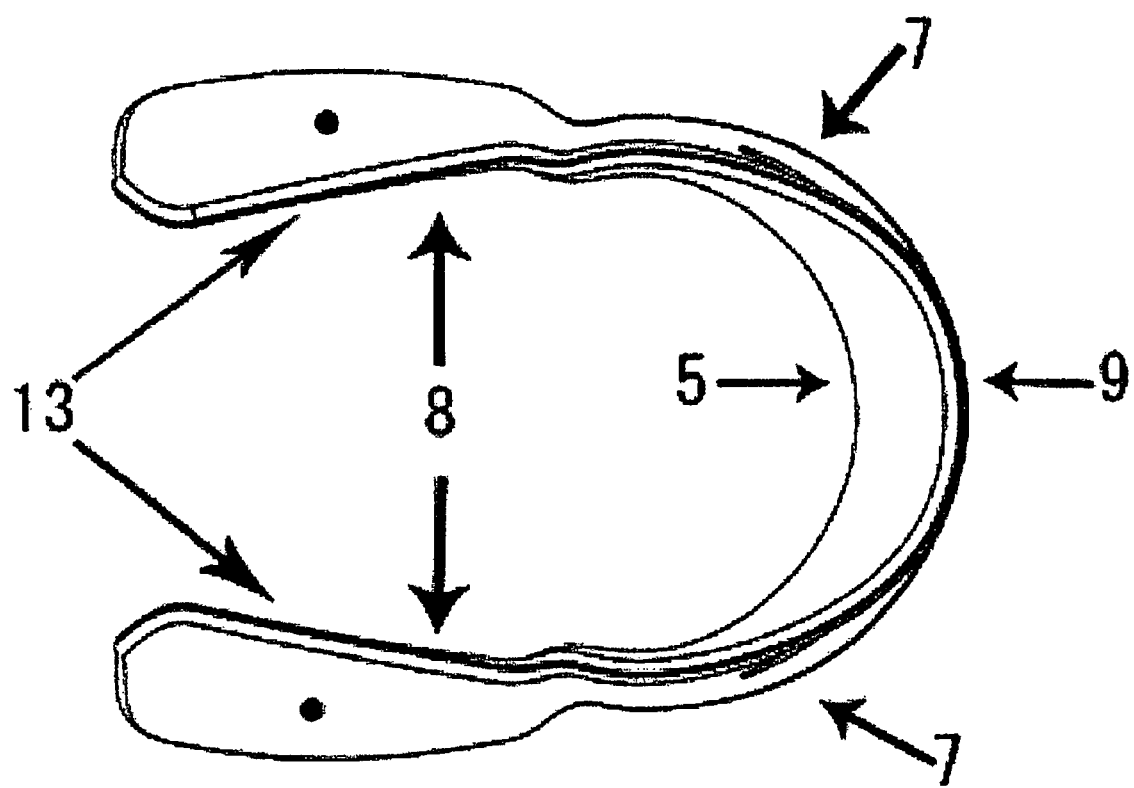
FIG. 7 shows a bottom view of Bone Structure Support (5, 7, 8, 9, 13).

The sleepy heads neck pillow of the invention will help people sleep while sitting up. The reason that the sleepy heads neck pillow of the invention is unique is because there is a bone structure support inside the pillow that is connected to the clip/strap system.

The pillow ("Sleepy Heads Neck Pillow") shape is unique because of the shape of the bone structure support that is fully incased in the pillow.

The bone structure support comprises three parts; a neck bone support, an arm bone, and an upper back bone support, which is made to give maximum support and great comfort to the head, neck and upper back. These three parts may be adjustable. In one embodiment, the bone structure support comprises a neck bone support configured to support the neck of the wearer, a pair of spaced arm bones extending from the neck bone support and configured to support the head of the wearer, and an upper back bone extending from the neck bone support and configured to support the upper back of the wearer.

The bone structure support comprising the neck bone support, the arm bone and the upper back bone support may be made of one piece. Alternatively, the bone structure support may be made of two or more pieces. For instance, the bone structure support may be separated to two pieces at the center of the upper back bone along a section line and the two pieces are combined together when being used.

Since there is a clip/strap system that is secured to the seat it gives optimum support to the head, neck, and upper back. The clip/strap system for a sleepy heads neck pillow is configured to engage a seat having a front, back and a top, and comprises adjustable seat clips, adjustable seat straps, detachable clips and a supportive seat brace, wherein said adjustable seat clips comprise two pieces; a back clip configured to set on said back and top of said seat, and a front clip configured to set on said front and top part of said seat and continues as the supportive seat brace, and wherein said adjustable seat strap system is connected to said adjustable seat clips and said detachable clips which is connected to said pillow, and said detachable clips can separate said pillow from said adjustable seat clips.

Sleepy Heads Neck Pillow of the present invention is also unique because there is a shoulder padding support built into the pillow.

Sleepy Heads Neck Pillow of the present invention comprises five different main parts; a pillow, a bone structure, an adjustable clip/strap system, shoulder support padding, a pillow cover and a clip system cover.

Sleepy Heads Neck Pillow of the present invention is explained in more detail by referring to the attached figures.

Adjustable Seat Clip (0)

The seat clip of the Sleepy Heads Neck Pillow is a unique clip system, because the clip closes automatically by the weight of the pillow when it is fixed on a seat. With the special smooth clip design it doesn't need any screws or other adjustment parts, the clip system will be easy to place on seats without damaging the seats.

In one embodiment of the present invention, the adjustable seat clip (0) comprises two pieces. One is a back seat clip configured to set on the back of the seat. The back seat clip may be enclosed in a strap which is connected to adjustable seat straps. The second piece is a front part of the clip (front clip) configured to set on the front part of the seat, and continues as a supportive seat brace. The front clip slides into the back clip or the back clip slides into the front clip, whereby the seat clip is made adjustable on the seat. The head weight on the pillow, which is connected to the adjustable seat straps, will cause the back seat clips to come forward, and make the clips secure on the seat.

Figure 9:
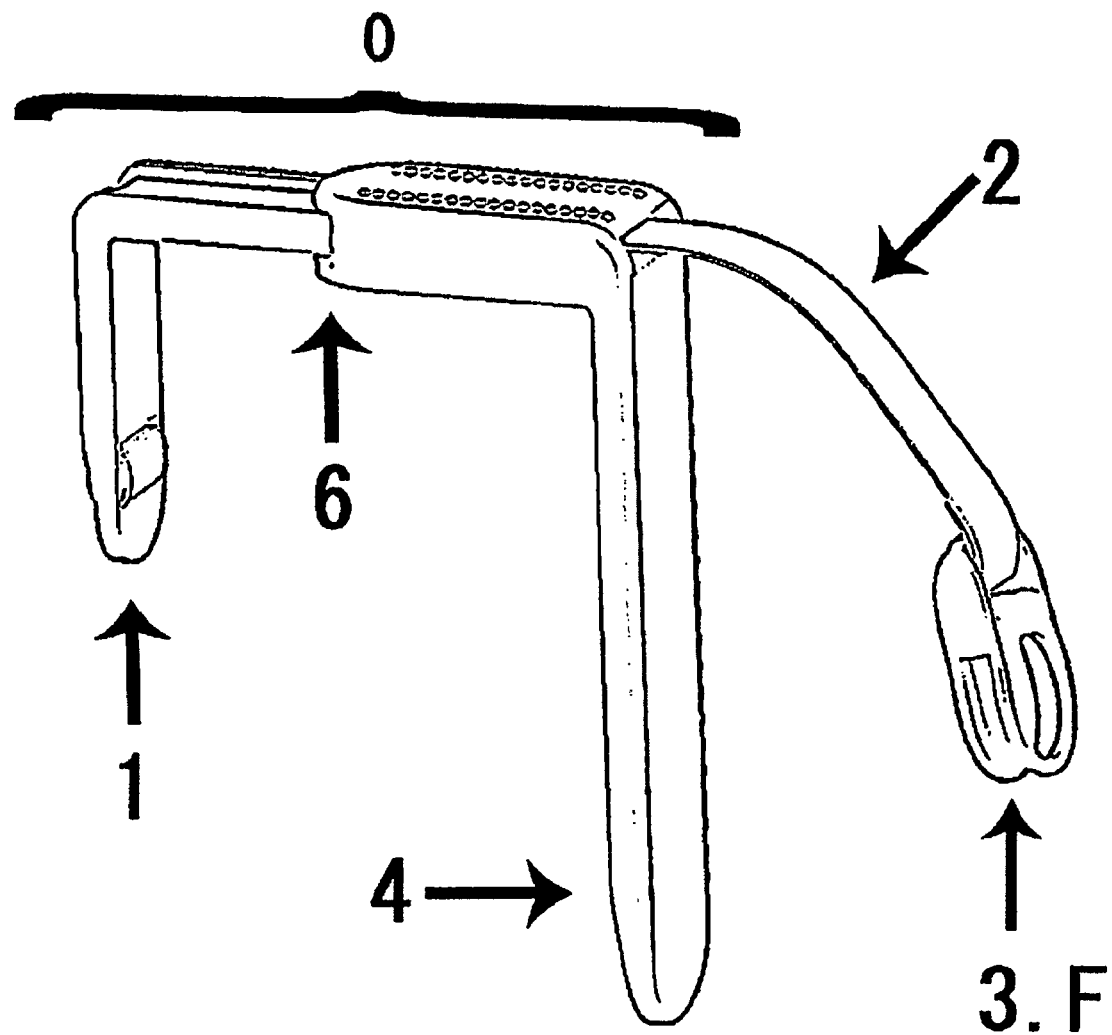
FIG. 9 shows Clip System (0, 1, 2, 3.F, 4, 6).
Figure 10:
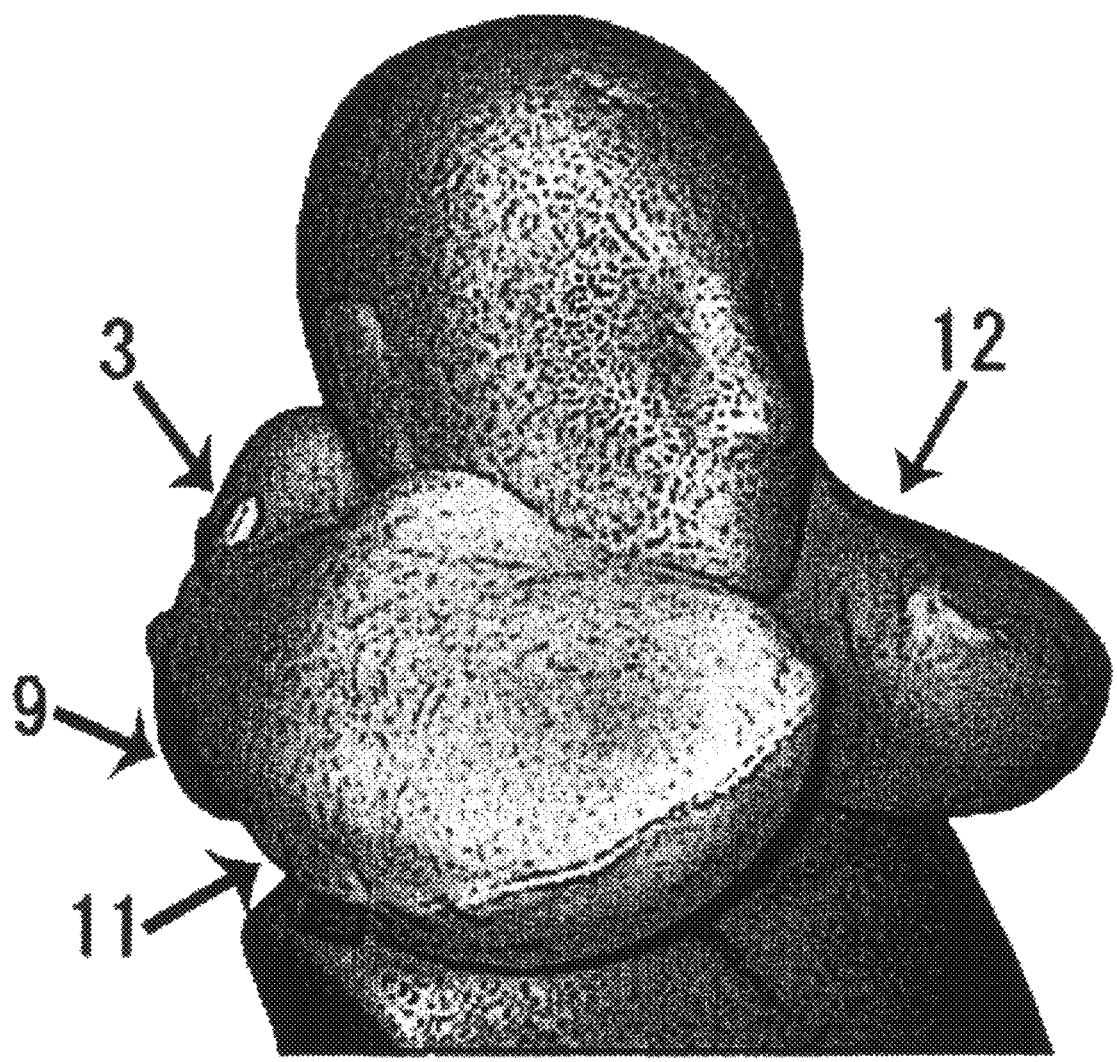
FIG. 10 shows Pillow and Pillow Cover at upside down position (3, 9, 11, 12).
Figure 11:
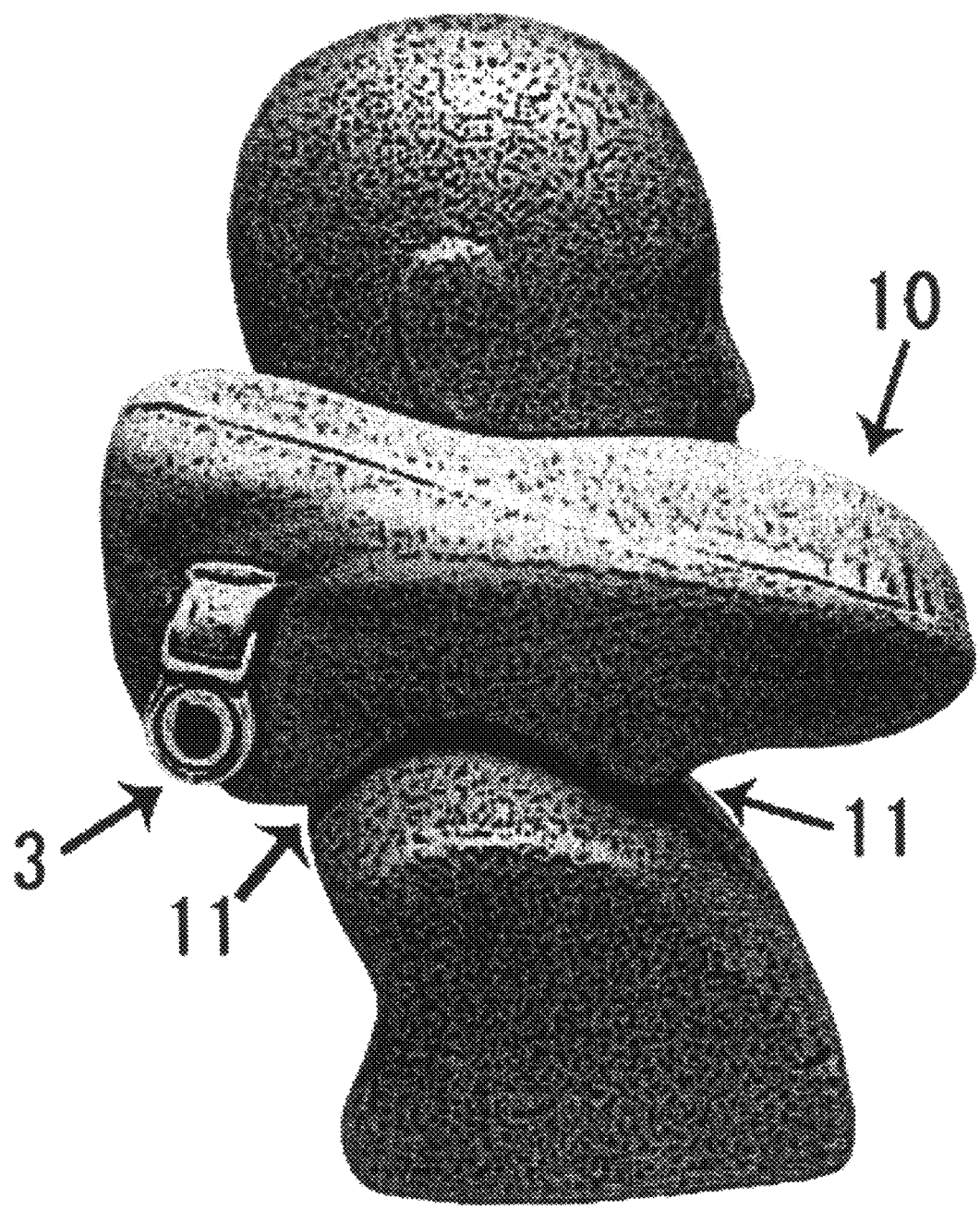
FIG. 11 shows a side view of Pillow and Shoulder Support Padding (3, 10, 11)
Figure 12:
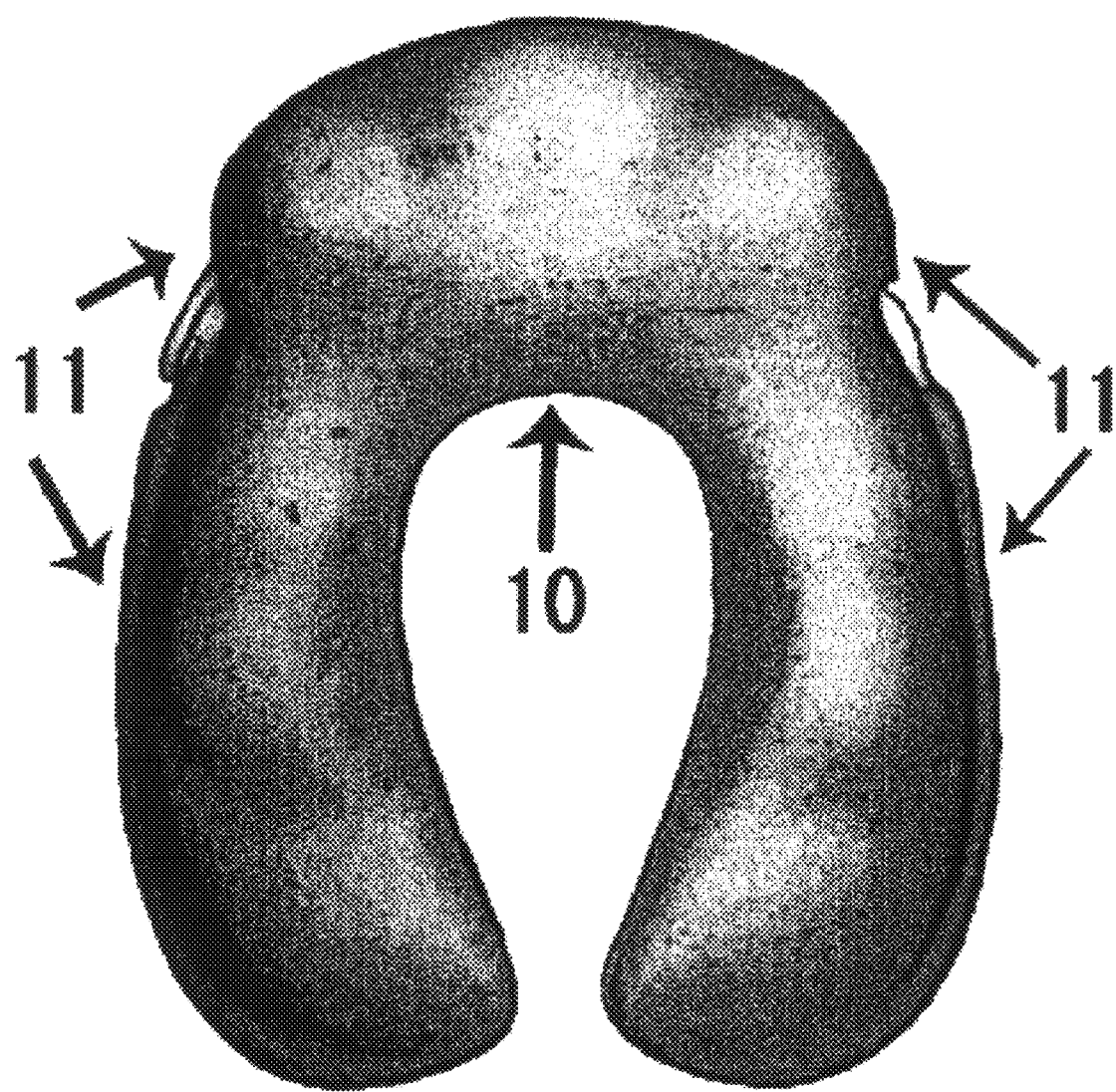
FIG. 12 shows a bottom view of Pillow (10, 11).
Figure 13:
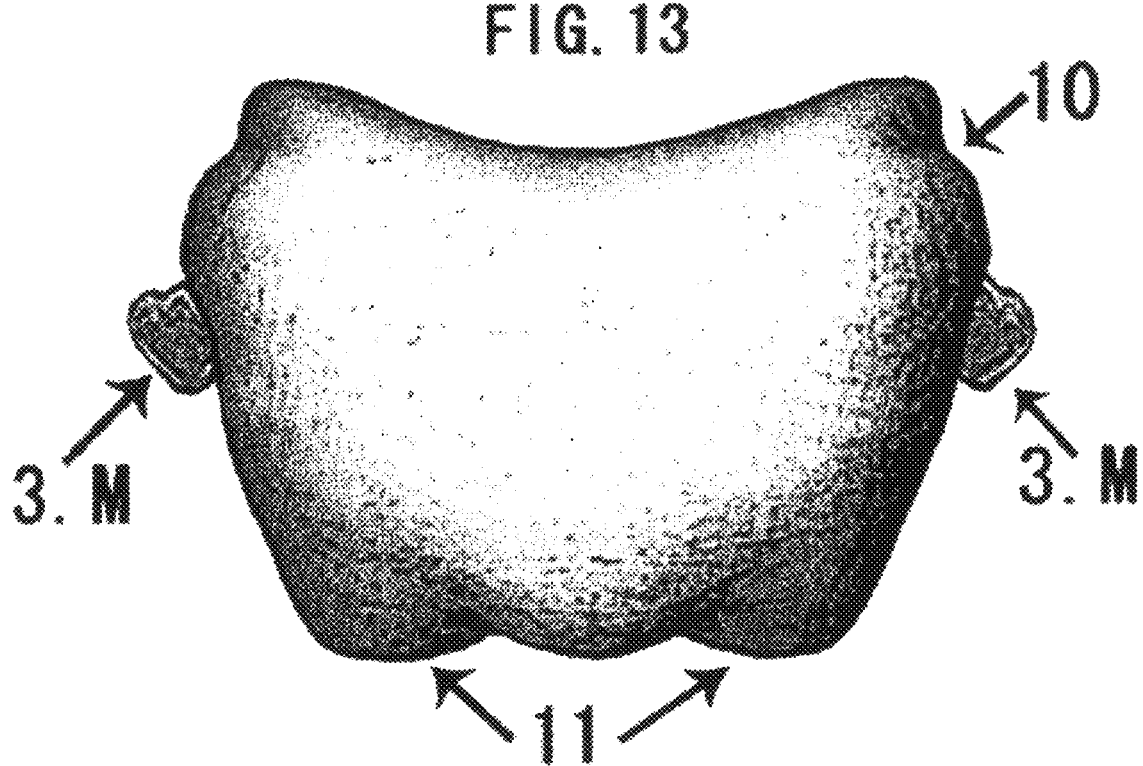
FIG. 13 shows a back view of Pillow without pillow cover and Bone Structure Support (3.M, 10, 11).
Figure 14:
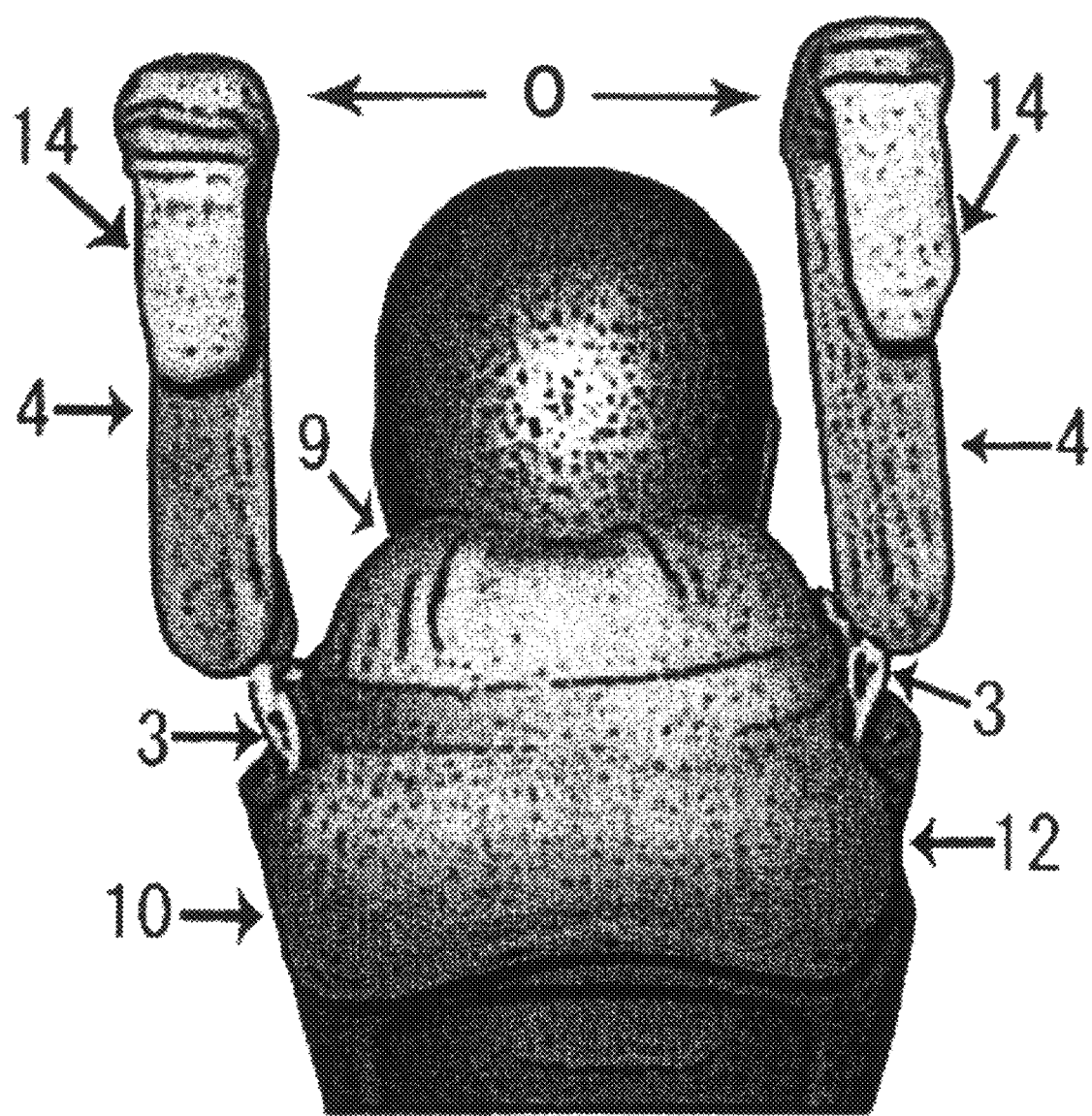
FIG. 14 shows a back view of Pillow at upside down Position with Bone Structure Support, Strap System Pillow Cover and Clip System Cover (0, 3.F, 4, 9, 10, 12, 14).

In another embodiment of the invention, the adjustable seat clip comprises three pieces. FIG. 9 shows non-limited example thereof. According to FIG. 9, the adjustable seat clip (0) comprises the back seat clip (1), the supportive seat brace (4), and the plug (6).

Back Seat Clip (1)

The back seat clip (1) is typically an upside-down L-shaped piece, configured to set on the back of the seat. It has a slot at the bottom tip so that a strap can be put through it. The back seat clip (1) has side edges so that the adjustable seat strap (2) can not move side to side, just back and forth. The adjustable strap (2) may be attached at any suitable part of the back seat clip (1), but it is preferably sown at the edge part of the back seat clip (1).

The back seat clip (1) has another slot on the underside of the top part thereof so that the Plug (6) can slide back and forth through it. The back seat clip (1) of the adjustable seat clip (0) slides into the back of the supportive seat brace (4). The adjustable seat clip (0) automatically moves forward, inward to the seat when the adjustable seat strap (2), which is connected to the detachable clip (3.F) that is connected to the pillow (10), is pulled down by the weight of the head on the pillow (10). The back seat clip (1) is made of strong durable slightly flexible hard plastic.

Supportive Seat Brace (4)

The supportive seat brace (4) is typically an upside-down L-shaped piece which goes on the top of the seat and down the front side of the seat. The top part of the supportive seat brace (4) has two parallel layers with a tunnel like space in between them so that the adjustable seat clip (1) and the adjustable seat straps (2) can slide through it. It has the plug (6) inside the top tip so that the two parts (1, 4) of the clip stays together. The supportive seat brace (4) is made of strong durable hard plastic. It gives extra support on the front of the seat and keeps the clips closed by the weight of the head on the pillow.

Plug (6)

Figure 8:
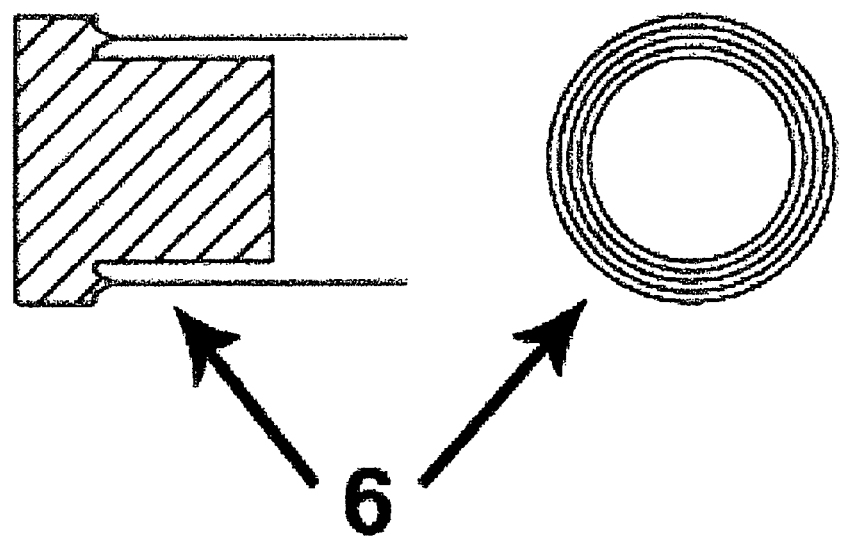
FIG. 8 shows Plug (6).

The plug (6), the third part of the clip system keeps the back seat clip (1) and the supportive seat brace (4) together. It is typically a small peg like, round shaped plug that is inside of the top tip part of the upside-down L-shaped supportive seat brace (4). (See FIG. 8.)

Adjustable Seat Straps (2)

The adjustable seat straps (2) are made of strong durable material. They are connected to the detachable seat clips (3.F, 3.M) and the adjustable seat clips (1). The adjustable strap (2) is enclosed in the supportive seat brace (4) which is connected to the back clip (1). They are made to be adjustable for any length (between 2 to 18 cm), or height of the person using the pillow.

Detachable Clips (3.F, 3.M)

The detachable clips (3.F, 3.M) are made of strong durable hard plastic. It is used to make Sleepy Heads Neck Pillow detachable from the adjustable clip/strap system.

Neck Bone Support (5)

The Neck Bone Support (5) is made of a strong durable hard plastic which the whole bone structure support that comprises the three parts; (5), (8), (9) which may be adjustable, is made of. It is the neck support of the bone structure of the pillow. It conforms, fits the shape of the neck which gives high support, and comfort to the neck of the pillow. The neck bone support is preferably C-shaped.

Arm Bone (8)

The Arm Bone (8) which may be adjustable is a part of the bone structure support that is extended over the shoulder from the neck bone support (5) which may be adjustable. It is an arm shape structure which gives support to the head when the head is resting on the side of the pillow (10).

Upper Back Bone Support (9)

The upper back bone support (9), a part of the bone structure support that is extended down the upper back support, gives extra support to the neck, and upper back. All of the three parts of the bone structure support which may be adjustable (5), (8), (9) combined together create a perfect balance, comfort to give the head, neck, and shoulders support with great stability on the pillow. The full bone structure support will be fully incased inside the pillow.

Strap Slots (7)

The Strap Slots (7) are for the straps of the clip/strap system (0), (1), (2), (3.F, 3.M), (4), (6) to be securely fastened on to the neck bone support (5) of the bone structure support (5), (8), (9).

Pillow (10)

The pillow (10) is made up of form fitting memory foam. The pillow is firm and delicate but because of the form fitting memory foam it also conforms to the shape of the head, neck, shoulders, and facial contour perfectly. The pillow is made so that the hardness of the bone structure support will not be able to be felt inside the pillow. The shape of the pillow (10) is made to match the shape of the bone structure support, it is a very supportive and comfortable pillow.

Shoulder Support Padding (11)

The shoulder support padding (11) is shaped to the contour of the shoulder, the shape of the shoulder support padding (11) is shaped to stay on the shoulders without falling off. The shoulder support padding (11) is made of form fitting memory foam that conforms to the shape of the shoulder, this support will give extra comfort and stability on the shoulders.

Pillow Cover (12)

The pillow cover (12) is made of a very soft stretchable material that will fit the pillow perfectly so that the shape of the pillow will appear, and the shape of the pillow cover (12) is the same shape as the pillow.

Placement Plug (13)

The placement plugs (13) are two small plugs on both sides of the middle of the arm bone (8). It is used to keep the bone structure support (5), (8), (9) in place in the steel mold during the process of the pillow molding injection.

Clip System Cover (14)

The clip system cover (14) is the cover for the adjustable seat clip (0), it is removable, washable, and can match the pillow cover color as a set.

On the market today, until now, no one has invented a heads neck pillow like the present invention.

Sleepy Heads Neck Pillow of the present invention has three different ways to use. The first use; upright, the top side of the pillow (10) will be used while awake, or resting while sitting up. There are many different uses; use while watching TV, watching sports, using the computer, playing games, gambling, to give support to people who have neck injuries, use in hospitals, and use during transportation (airplane, train, bus, car, etc.).

The second use because of a very high support; the bottom side of the pillow (10) will be used when sleeping while sitting up. Use the bottom side of Sleepy Heads Neck Pillow during transportation (airplane, train, bus, car, etc.) or anytime, anywhere while sleeping while sitting up. Sleepy Heads Neck Pillow is designed to be reversible, the top part and the bottom part can be used in two different ways for the two different uses. As the third use; use Sleepy Heads Neck Pillow with the adjustable clip/strap system on seats for extra support for the pillow.

The Sleepy Heads Neck Pillow of the invention will be useful to insurance companies because it will provide their customers with extra safety which will reduce the risk of neck injuries, therefore saving money for the insurance companies, and their customers. Whiplash victims can also use Sleepy Heads Neck Pillow, the invention can ease their pain because it will give their neck support and comfort. Airline companies can also build Sleepy Heads Neck Pillow of the invention into the airplane seats so that the passengers will be able to sleep sitting up during flight with great comfort. The airlines companies can also rent Sleepy Heads Neck Pillow, the invention on their flights for their passengers.

Sleepy Heads Neck Pillow of the invention may be made in five different sizes. X-Small (infant), Small (child), Medium (Adult), Large (Adult), X-Large (Adult). The pillow structure and shape may be exactly the same, only the size may be different.

FULL LISTING OF ITEMS

0. Adjustable Seat Clip
1. Back Seat Clip
2. Adjustable Seat Strap
3.M, 3.F Detachable Clip
4. Supportive Seat Brace
5. Neck Bone Support
6. Plug
7. Strap Slots
8. Arm Bone
9. Upper Back Bone Support
10. Pillow
11. Shoulder Support Padding
12. Pillow Cover
13. Placement plug
14. Clip System cover

The invention claimed is:

1. A pillow configured to be positioned on the shoulders of a wearer and support the neck of the wearer, comprising: a bone structure support fully incased inside said pillow, said bone structure support comprising a neck bone member having a top edge, a bottom edge, a left edge and a right edge, which is configured to support the neck of the wearer; a first arm bone and a second arm bone extending respectively from the left and right edges of said neck bone member and configured to support the head of the wearer, and an upper back bone support extending down at an angle from the bottom edge of said neck bone member so that the upper back bone support is configured to give extra support to the neck and the upper back of the wearer, wherein said first arm bone has a first arm bone upper portion, a first arm bone lower portion, a first arm bone inner side and a first arm bone outer side, said first arm bone upper portion being angled with respect to said first arm bone lower portion such that a portion of said first arm bone inner side faces upwardly; and said second arm bone has a second arm bone upper portion, a second arm bone lower portion, a second arm bone inner side and a second arm bone outer side, said second arm bone upper portion being angled with respect to said first arm bone lower portion such that a portion of said second arm bone inner side faces upwardly, the lower portion of the first arm bone being spaced from the lower portion of the second arm bone a distance smaller than the distance that the upper portion of the first arm bone is spaced from the upper portion of the second arm bone.

2. The pillow according to claim 1, further comprising a strap system fixed to said bone structure support, said strap system comprising a clip.

3. The pillow according to claim 1 or 2, wherein said neck bone member is C-shaped.

4. The pillow according to claim 2, wherein said strap system comprises a supportive adjustable strap which is connected to the clip, said adjustable strap being fixed to said bone structure support.

5. The pillow according to claim 1, further comprising shoulder support padding on said pillow configured to contact the wearer's shoulders.

6. The pillow according to claim 1, further comprising shoulder support padding on said pillow configured to contact the wearer's shoulders.

7. The pillow according to claim 1, further comprising a pillow cover covering said pillow.

8. The pillow according to claim 1, which is reversible wherein the top part of the pillow is used when being awake, to give support and comfort while using a computer, watching TV, playing a video game, and bottom part of the pillow is used when sleeping while sitting up.

9. The pillow according to claim 1, wherein the neck bone member, the first and second arm bones and the upper back bone support are adjustable.

10. The pillow according to claim 1, which is reversible wherein the top part of the pillow is used when being awake, to give support and comfort while using a computer, watching TV, playing a video, and bottom part of the pillow is used when sleeping while sitting up.

* * * * *